(12) United States Patent
Chiou (10) Patent No.: US 6,608,172 B1
(45) Date of Patent: Aug. 19, 2003

(54) ISOLATION OF IGY (ΔFC) ANTIBODIES

(75) Inventor: Victor Chiou, Taichung (TW)

(73) Assignee: Good Biotech Corporation (TW)

( * ) Notice: Subject to any disclaimer, the term of this patent is extended or adjusted under 35 U.S.C. 154(b) by 0 days.

(21) Appl. No.: 09/591,665

(22) Filed: Jun. 9, 2000

(51) Int. Cl.$^7$ .......................... G01N 33/08; C07K 16/02; C07K 17/02; C07K 1/14
(52) U.S. Cl. ..................... 530/4.13; 530/389.1; 530/861
(58) Field of Search .............................. 530/413, 389.1, 530/861

(56) References Cited

U.S. PATENT DOCUMENTS

| | | | |
|---|---|---|---|
| 4,550,019 A | | 10/1985 | Polson |
| 5,340,923 A | | 8/1994 | Carroll |
| 5,367,054 A | * | 11/1994 | Lee et al. |
| 5,585,098 A | | 12/1996 | Coleman |
| 5,601,823 A | | 2/1997 | Williams et al. |
| 5,728,813 A | * | 3/1998 | Lyman et al. |
| 5,814,477 A | * | 9/1998 | Williams et al. |
| 5,976,519 A | | 11/1999 | Nojiri et al. |

FOREIGN PATENT DOCUMENTS

| | | |
|---|---|---|
| JP | 64-38098 | 2/1989 |

OTHER PUBLICATIONS

Higgins et al, Veterinary Immunol and Immunopathology 44: 169–180, 1995.*
Otani et al, Lebsensm Wiss U Technol 24: 152–158, 1991.*
Akita et al., Comparison of Four Purification Methods for the Production of Immunoglobulins from Eggs Laid by Hens Immunized with an Enterotoxigenic E. coli Strain, J. of Immunological Methods 160:207–214, 1993.
Akita et al., "Immunoglobulins from Egg Yolk: Isolation and Pufication", J. of Food Science 57:629–634, 1992.
Akita et al., "Production and Purification of Fab' Fragments from Chicken Egg Yolk Immunoglobulin Y (IgY)", J. of Immunological Methods 162:155–164, 1993.
Brussow et al., "Bovine Milk Immunoglobulins for Passive Immunity to Infanile Rotavirus Gastroenteritis", J. of Clinical Microbiology 25:982–986, 1987.
Chr. et al., "Eggs: Conveniently Packaged Antibodies. Methods for Purification of Yolk IgG", J. of Immunological Methods 46:63–68, 1981.
Gottstein et al., "Egg Yolk Immunoglobulin Y as an Alternative Antibody in the Serology of Echinococcosis", Parasitenkunde 71:273–276, 1985.
Grey, "Duck Immunoglobulins. I. Structural Studies on a 5.7S and 7.8S γ–Globulin", J. of Immunology 08:811–819, 1966.
Hassl et al., "Purification of Egg Yolk Immunoglobulins A Two–step Procedure Using Hydrophobic Interaction Chromatography and Gel Filtration", J. of Immunological Methods 110:225–228, 1988.

Hatta et al., "Separation of Phospholipids from Egg Yolk and Recovery of Water–Soluble Proteins", J. of Food Science 53:425–431, 1988.
Higgins, "Precipitating Antibodies of the Duck (Anas platyrhynchos)", Comp. Biochem. Physiol. 93B:135–144, 1989.
Lamoyi, "[62] Preparation of F(ab')$_2$ Fragments from Mouse IgG of Various Subclasses", Methods In Enzymology 652–663.
Litman et al., "Active Sites of Turtle and Duck Low Molecular Weight Antibody to 2'4' Dinitrophenol", Immunochemistry 10:323–329, 1973.
Magor et al., "Structural Relationship Between the Two IgY of the Duck, Anas Patrhynchos: Molecular Genetic Evidence", J. of Immunology 149:2627–2633, 1992.
Muratsugu et al., "Adsorption and Desorption of F(ab')$_2$Anti–hIgG on Plasma–Polymerized Allhylamine Thin Film: The Application of the Film to Immunoassay", J. of Colloid and Interface Science 147:378–386, 1991.
Ortega–Vinuesa et al., "Particle Enhanced Immunoaggregation of F(ab')$_2$ Molecules", J. of Immunological Methods 190:29–38, 1996.
Polson et al., "Isolation of Viral IgY Antibodies from Yolks of Immunized Hens", Immunological Communications 9:475–493, 1980.
Tacket et al., "Protection by Milk Immunoglobulin Concentrate Against Oral Challenge with Enterotoxigenic Escherichia coli", The New England Journal of Medicine 318:12401243, 1988.
Toth et al., "Humoral Immune Response of the Duck to Duck Hepatitis Virus: Virus–Neutralizing vs. Virus–Precipitating Antibodies", Avian Diseases 25:17–28, 1980.
Unanue et al., "Experimental Glomerulonephritis V. Studies on the Interaction of Nephrotoxic Antibodies with Tissues of the Rat", Publication No. 98 from the Division of Experimental Pathology, Scripps Clinic and Research Foundation, La Jolla, 697–714, 1965.
Zimmerman et al., "Structural Studies on the Duck 5.7S and 7.8S Immunoglobulins", Biochemistry 10:482–488, 1971.

* cited by examiner

Primary Examiner—Christina Chan
Assistant Examiner—Phuong N Huynh
(74) Attorney, Agent, or Firm—Fish & Richardson P.C.

(57) ABSTRACT

The present invention relates to a method for the preparation and purification of IgY(ΔFc) antibody from avian yolk, generally comprising the steps of immunization of a fowl hen with an antigen, a partial purification of the whole antibodies from the eggs laid by the hen, and an immunoaffinity purification of the antibodies raised against the antigen, in which the binding of the antibodies with the antigen in the immunoaffinity purification step is conducted at pH within a range of 4–7 and under an ionic strength of lower than 50 mM. The present invention also relates to the IgY(ΔFc) antibody produced thereby and various uses of the novel IgY(ΔFc) antibody.

11 Claims, 6 Drawing Sheets

ISOLATION OF IGY (ΔFC) ANTIBODIES

BACKGROUND OF THE INVENTION

1) Field of the Invention

The present invention relates to a method for the preparation and purification of IgY(ΔFc) antibody from avian yolk, and the IgY(ΔFc) antibody produced thereby. The present invention also relates to uses of the novel IgY(ΔFc) antibody for quantitatively or qualitatively analyzing an etiological agent of interest.

2) Description of the Related Art

Antibodies are used widely in many biological investigations and clinical applications. Sera obtained from hyperimmunized mammalians are the most common source of polyclonal antibodies. Antibodies derived from such immune sera belong to a group of proteins called 'immunoglobulins,' among which the immunoglobulin G (IgG) is the most abundant. The IgG molecule consists of three domains, namely two Fab regions and one Fc region. The Fab portion involves mainly in antigen binding. The Fc portion, though having no ability to bind with an antigen, directs several biological activity of an antibody, such as complement fixing and Fc receptor binding.

In the art of immunodiagnostics, an intact IgG molecule is not suitable for use in detection systems and immunological assays involving mammalian sera since the Fc region on an IgG molecule is capable of binding to Fc receptors, activating the complement system, and reacting with rheumatoid factor in mammalian sera. Removal of the Fc portion of an IgG molecule frequently lead to a reduction in the interference (E. Lamoyi, *Methods in Enzymology* 121:652–663. (1986)).

Some of the suggested uses of antibody in immunotherapy include treating patients with intoxicated bacterial toxins or snake venoms (see, for example, U.S. Pat. Nos. 5,340,923 and 5,601,823), and protection of neonatal piglets against fatal enteric colibacillosis (see, for example, H. Brussow et al., *J. Clin. Microbiol.* 25:982 (1987); and C. O. Tacket et al., *New Eng. J. Med.* 318:1240 (1988)). Since the Fc fragment of an antibody molecule is known to be the most antigenic portion of the immunoglobulin (E. M. Akita et al., *J. Immunol. Methods.* 162:155–164 (1993)), cleavage of the same which results in the formation of an F(ab')$_2$ fragment will reduce significantly a number of potential allergenic sites on the immunoglobulin molecule and is thus beneficial to human or an animal administered with the immunoglobulin.

Recently, the divalent F(ab')$_2$ antibody fragment has been shown to be more useful in the immunodiagnostic tests (M. Muratsugu et al., *J. Colloid Interface Sci* 147:378 (1991); and J. L. Ortega-Vinuesa et al., *J. Immunol Methods* 90:29 (1996)) and more suitable for development of the immunoassays involving mammalian sera than the parent IgG.

The F(ab')$_2$ antibody fragment, however, has not found widespread use in clinical immunodiagnostic kits as one might expect. This may be attributed to the difficulties and cost-ineffectiveness of large scale production of the F(ab')$_2$ fragments, which is conventionally made by pepsin digestion of IgG and subsequent purification via chromatography.

Ducks and their phylogenetically close relatives and some reptiles, such as turtles, have three kinds of serum immunoglobulins: a macromolecular immunoglobulin IgM (800 kDa in duck), and two isoforms of low molecular weight IgG with sedimentation coefficients of 7.8S (in duck, 180 kDa) and 5.7S (in duck, 130 kDa), respectively. (E. R. Unanue etal., *J. Exp. Med.* 121:697–714 (1965); H. M. Grey, *J. Immunol* 98:811–819 (1967); and B. Zimmerman et al., *Biochemistry* 10:482–448 (1971)). Avian IgG is oftentimes called IgY due to their existence in egg yolk. The 5.7S IgY, constituted with shorter heavy chains, is structurally and antigenically similar to the F(ab')$_2$ fragment of the 7.8S IgY (FIG. 1), and this fact leads to the nomenclature of IgY (equivalent to 7.8S IgY) and IgY(ΔFc) (equivalent to 5.7S IgY) to represent both isoforms of IgY (K. E. Magor et al., *J. Immunol.* 149:2627–2633 (1992)).

Studies conducted in the infected or experimentally immunized birds showed that duck antibodies are deficient in a number of biological effector functions, including complement fixation and Fc receptors binding, without sacrificing their binding activity to corresponding antigens (G. W. Litman et al., *Immunochemistry* 10:323 (1973); and T. E. Toth et al., *Avian Dis.* 25:17–28 (1981)). This may reasonably result from the apparent lack of Fc-equivalent region of the IgY(ΔFc) antibody that constitutes the quantitatively major component of duck antibody response. It is thus believed that the IgY(ΔFc) antibody, which appears to be a structural and functional analog of the F(ab')$_2$ fragment, would provide magnificent advantages in immunological uses, if a promising process for manufacturing the antibody could be found, and the appropriate physical requirements for its activity could be identified.

Avian yolk antibodies have been reported to exhibit useful properties for both research and clinical applications as mammalian antibodies do (see, for example, U.S. Pat. Nos. 5,340,923; 5,585,098; 5,601,823; and 5,976,519). Egg yolks derived from a laying hen is inexpensive and more convenient and safer to handle as compared to the hyperimmunized mammalian sera. More importantly, yolk antibodies are able to stand up to the scrutiny under modern animal protection regulations (A. Polson et al., *Immunol. Commun.* 9:475 (1980); and B. Gottstein et al.). These facts suggest a potential use of egg yolk as a commercial source of antibodies.

Efforts have been made to isolate and purify IgY from egg yolks. For instance, materials, including agar, pectin (Japanese Kokai No. 64-38098 published in Feb. 8, 1989), dextran sulfate (J. C. Jensenius et al., *J. Immunol. Methods* 46:63 (1981)), natural gums (H. Hatta et al., *J. Food Science* 53:425(1988)) and polyethyl glycol (PEG) (A. Polson et al., *Immunol. Invest.* 14:323 (1985); see also U.S. Pat. No. 4,550,019 issued to A. Polson) were used to precipitate non-aqueous bio-molecules, mainly lipids and yolk granules, to thereby harvest a water soluble phase containing abundant yolk antibodies. A. Hassl et al. developed a two-step chromatographic process, comprised of hydrophobic interaction chromatography and size exclusive chromatography, for further isolation of yolk antibodies from a PEG-purified fraction (A. Hassl and H Aspock, *J. Immunol. Methods* 110:225 (1988)). Akita et al. described an improved method for isolating IgY, in which yolk antibodies were extracted from chick eggs by diluting the egg yolks with a large volume of water and subjecting the resultant supernatant to size exclusive chromatography and/or ion exchange chromatography (E. M. Akita et al., *J. Immunol. Methods.* 160:207 (1993); and E. M. Akita and S. Nakai, *J. Food Sci.* 57:629 (1993)).

However, all these studies and patents only focus on the isolation of the entire population of yolk antibodies (which includes at least IgY and IgY(ΔFc)) from avian eggs, rather than on the purification of IgY(ΔFc) antibody alone. Moreover, since the IgY(ΔFc) antibody is only present in the birds belonging to Order Anseriformes, including duck and goose, the isolation methods implemented on the galliform birds, such as chicken and turkey, provide no suggestion of a successful purification of IgY(ΔFc) antibody.

In 1989, Higgins tried to prepare the antibodies from hyperimmunized duck sera, but the antibodies affinity-purified at pH 8.0 and 0.5 M NaCl generally failed to exhibit effective precipitation or agglutination reactions (D. A. Higgins, *Comp. Biochem. Physiol.* 93B:135–144 (1989)). The optimal pH value for forming duck antibody precipitins, as Higgins alleged in the literature, ranges from pH 8.5 to pH 9.05. Since then, no critical study regarding the isolation of the IgY(ΔFc) antibody and its potential uses has been reported.

Therefore, there is a need in the art for a rapid, cost-effective, high-throughput process that provides easy isolation of the desired IgY(ΔFc) antibody from the antibody pool while maintaining its activity. Furthermore, there is a need in the art for a substantially purified IgY(ΔFc) which acts as a new type of F(ab')$_2$ antibody for various immuno-diagnostic and immunotherapeutic uses.

SUMMARY OF THE INVENTION

An extensive research has been conducted to fulfill the industrial requirements for yolk antibodies as indicated above. Surprisingly, we found that a successful isolation of IgY(ΔFc) antibodies from avian yolks can be readily accomplished through a simplified procedure under an optimal binding condition for the interaction between the antigen and antibody during immunoaffinity purification. By way of the process according to the present invention, a new type of F(ab')$_2$ antibodies, i.e., the essentially purified IgY(ΔFc), can be easily manufactured with high yield in an economic manner, and the IgY(ΔFc) antibodies so produced are ready for a wide variety of immunological uses.

Accordingly, an object of the present invention is to provide a process for preparing IgYΔFc antibodies from eggs laid by hens. The process generally comprises the steps of immunization of a fowl hen with an immunogen, a partial purification of the whole antibodies from the eggs laid by the hen, and an immunoaffinity purification of the antibodies raised against the immunogen, in which the binding of the antibodies with the immunogen/antigen in the immunoaffinity purification step is conducted in an environment of weak acid and low ionic strength. Specifically, the antibody-antigen interaction is conducted at pH within a range of 4–7 and under an ionic strength of lower than 50 mM, to obtain an optimal result.

The present invention thus provides a process for preparing IgYΔFc) from egg yolk, which comprises the steps of:

(a) immunizing a fowl hen with a selected antigen so that fowl antibodies elicited against the antigen are accumulated in egg yolk;

(b) collecting egg yolk of the immunized hen and removing non-aqueous bio-molecules and granules therefrom to thereby obtain a water-soluble fraction containing egg yolk antibodies;

(c) passing the water-soluble fraction through an inert support matrix immobilized with the antigen thereon at pH within a range of 4–7 and under an ionic strength of lower than 50 mM to allow the formation of immunocomplexes of the immobilized antigen and the yolk antibodies; and (d) dissociating and eluting out the yolk antibodies from the immobilized antigen.

Another object of this invention is to provide a novel IgY(ΔFc) antibody manufactured by the process according to this invention. It is still another object of the invention to provide the clinical and research uses of the IgY(ΔFc) antibody so produced. In addition to the cost-effectiveness and ease of preparation, the IgY(ΔFc) antibody according to the present invention has advantages of being inactive to the complement system and rheumatoid factors in mammalian sera, and having poor cross-reactivity to mammalian IgG, and is thus particularly suitable for use in immunological assays involving mammalian sera with minimal interference. As known by those skilled in the art, the antibody can be present in the form of a single reagent for clinical, research and other applications, or included in a commercial kit as an active component.

It is another specific object of the invention to provide a reagent for immunoassay of an etiological agent of interest, comprising an IgY(ΔFc) antibody manufactured by the process according to this invention.

A still another object of this invention is to provide a method of immunoassay and a commercial kit for conducting said immunoassay, in which an antibody, preferably an IgY(ΔFc) antibody purified according to the invention, against an etiological agent is incubated in the presence or absence of the etiological agent of interest under an optimal condition for binding to the etiological agent, to thereby quantitatively or qualitatively analyzing the etiological agent. According to the present invention, the optimal condition is at pH within a range of 4–7 and under an ionic strength of lower than 50 mM.

BRIEF DESCRIPTION OF THE DRAWINGS

The above and other objects and features of the present invention will become apparent with reference to the following description of the preferred embodiments taken in conjunction with the accompanying drawings, in which.

DETAILED DESCRIPTION OF THE INVENTION

In accordance with the present invention, a process for preparing IgY(ΔFc) from egg yolk may generally comprise the steps of: (1) immunization of a laying hen; (2) partial purification of egg yolk; (3) immuno-affinity purification; and (4) elution of the antibody.

(1) Immunization of a Laying Hen

A female anseriform bird, preferably a duck or a goose, was immunized with an antigen to elicit the production of an antibody or antibodies of interest. The antigen includes but is not limited to a microorganism, such as a pathogenic or non-pathogenic bacterium, virus, fungus, protozoa, nematode and the like, a naturally occurring or synthetic protein, such as a toxin or a hormone, a naturally occurring or synthetic oligopeptide, a recombinant protein or a fragment thereof, and any other material capable of stimulating antibody production, and a combination thereof.

It is contemplated that the antibody can be obtained from either the bird serum or the eggs laid by the bird. However, as described above, collection of the antibody from the egg is usually preferred on account of the cost. The laying hen transfers both isotypes of IgY and IgY($\Delta$Fc) from serum to the egg yolk. In principle, a duck egg contains about 1–4 mg IgY/ml and about 3–12 mg IgY($\Delta$Fc)/ml in the yolk and, therefore, each egg could possibly provide 15–80 mg IgY and 45–240 mg IgY($\Delta$Fc). The large volume of egg yolk produced vastly exceeds the volume of the serum that can be safely obtained from the birds over any given time period. In addition, extraction of yolk antibodies can be performed on a large scale without costly investment.

The techniques for immunization of a hen with selected antigens are well known to those in the art. It is not intended to direct to a particular mode of immunization. The present invention contemplates all modes of immunization, which may be performed by inoculation with antigen by appropriate routes, including subcutaneous, intracutaneous, intramuscular, and intravascular injection.

Preferably, a suitable adjuvant is administered in conjunction with the antigen to enhance the immune response. More preferably, a dose of Complete Freund's Adjuvant can be used alone or optionally in combination with a follow-up dose of Incomplete Freund's Adjuvant. It has been found that the use of a suitable adjuvant is highly effective in maintaining a high antibody titer in the eggs of an immunized hen for a long period, thereby making it possible to produce the desired antibody efficiently.

During immunization, a female hen is initially inoculated with the antigen on day zero and subsequently receives the antigen in intervals thereafter. The interval between the initial immunization and the first booster administration and between individual booster administration depends on the specific characteristics of the antigen and is preferably at least two weeks. Usually 10 weeks following the initial immunization, a large quantity of reactive antibody against the antigen is produced within the body of the hen, and the egg laid by the hen. The existence and the titer level of the specific antibody against the antigen in the sera and eggs of the hen can be confirmed by a number of methods known in the art.

(2) Partial Purification of Egg Yolk

A procedure of partial purification is carried out to remove the majority of the non-aqueous bio-molecules and granules and preferably the majority of irrelevant proteins in the egg yolk. Any conventional method effective to achieve such a purpose is useful in the present invention, exemplary of which includes the use of PEG, dextran sulfate or a natural gum, such as sodium alginate, carrageenan and xanthan gum, to coprecipitate the undesired substances, and the use of an aqueous buffer or water to obtain an aqueous phase rich with antibodies.

In a preferred embodiment of the present invention, the yolk is firstly separated from the egg white, and then washed with distilled water to remove as much albumen as possible. The vitelline membrane encasting the yolk is punctured, and the separated yolk fraction is then diluted with an effective amount of an aqueous buffer or water to form a suspension of the egg yolk. Preferably, the collected egg yolk is diluted with an aqueous buffer solution or distilled water in a ratio of about 1:2 to about 1:40 v/v, and more preferably, in a ratio of about 1:5 to about 1:30 v/v. pH value is reported to be a critical factor during the stage of partial purification (E. M. Akita and S. Nakai, *J. Food Sci.* 57:629 (1993)). For the best recovery of yolk antibodies, pH is preferably set within a range of about 5–7. Desirably, the temperature in this step is within a range of about 0° C.–60° C. The suspension of the egg yolk is gently agitated to form a homogenous mixture, and then allowed to stand for a period of time sufficient to form the aqueous and non-aqueous phases. The water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitant by decanting, suctioning, or other like methods known in the art.

Optionally but preferably, the yolk supernatant is further treated with a high concentration of a non-denaturing salt to induce precipitation of the antibodies. Examples of the salts useful for precipitation of the yolk antibodies include but is not limited to NaCl, $Na_2SO_4$, $(NH_4)_2SO_4$, KCl, $CaCl_2$, and $MgSO_4$. Preferred are $Na_2SO_4$ and $(NH_4)_2SO_4$. The salt concentration for precipitating antibodies is important and, depending on the type of the salt, is usually present in an amount of higher than 15% and lower than 35% by weight, preferably in a range between 20% and 30% by weight of the salt, on the basis of the final volume of the yolk supernatant.

(3) Immuno-affinity Purification

As used herein, the term "immunoaffinity purification" or "immunoaffinity chromatography" is directed to a type of separation method based on the adsorption characteristics of antibodies for a specific antigen. That is, the antibodies that bind to a specific antigen under a particular condition are separated from the unbound antibodies under that condition. The present invention contemplates the use of immunoaffinity purification to eliminate irrelevant proteins, including proteins other than immunoglobulins and non-antigen-binding immunoglobulin. More importantly, the immunoaffinity purification procedure according to the present invention dramatically accomplishes a main object of the present invention, i.e., essential separation of the desired IgY($\Delta$Fc) antibodies from the whole population of yolk antibodies including IgY.

According to the present invention, the immunoaffinity purification is conducted by use of an "antigen matrix" comprised of antigen immobilized onto an insoluble support. The type of the support is not critical to the immunoaffinity purification of the invention. Any conventional support material suitable for the covalent attachment of an antigen and inert to the interaction between the desired antibody and the antigen immobilized thereon is useful. Usually, the support is made of crosslinked agarose or corsslinked dextran, such as the CNBr-activated SEPHAROSE™ 4B commercially available from Pharmacia.

The antibodies partially purified in stage (2) is dissolved in a "binding buffer" and applied onto the antigen matrix, so that the immuno-complexes of the immobilized antigen and the yolk antibodies are formed. Any buffer system inert to the antigen-antibody interaction and effective to maintain the desired binding condition is useful in the present invention. Preferably, the binding buffer is selected from the group consisting of a phosphate buffer, an MES (2-[N-morpholino] ethanesulfonic acid) buffer and a bis-Tris buffer, among which an MES buffer at a concentration of 20 mM is the most preferred.

The terms "flow through" as used herein is intended to represent the antibody solution passing through the antigen matrix, which contains the majority of non-binding substances.

Based on the general knowledge in the art of immunoaffinity purification, formation of an immuno-complex at a pH of about 7–9 and under an ionic strength higher than 150 mM is usually recommended. Under this condition, however, yolk antibodies, in particular those derived from the egg yolk of a duck, seem to less readily bind with the antigen immobilized on the chromatographic supports in a maximal manner. The active antibodies were still present in the flow through. In the process according to the invention, the condition used for immunoaffinity purification of IgY (ΔFc) antibody is unique. In the invention, antibodies prepared from yolks bind optimally in an environment of weak acid and low ionic strength, i.e., at pH within a range of 4–7 and under an ionic strength of lower than 50 mM. Preferably, the antibodies were allowed to interact with the immobilized antigen at pH within a range of 5–6 and more preferably within a range of 5.6–5.8. Under the binding condition disclosed in the present invention, no detectable active antibody was found in the flow through.

(4) Elution of the Antibody

As used herein, the term "eluent" is directed to a chemical solution capable of dissociating antibody bound to the antigen matrix that passes through the antigen matrix and comprises an "eluate." In general, the elution condition to break yolk antibody-antigen interaction is milder than mammalian antibody-antigen interaction.

Typically, an eluent buffered at a pH of lower than 4 or higher than 8 works well for elimination of IgY(ΔFc)-antigen interactions. The eluents having an extreme pH value, however, are normally not recommended since such a severe condition would possibly cause serious loss of the antigen binding ability of the antibodies.

Alternatively, the eluent containing a high concentration of a chaotropic agent can be utilized in the present invention. As used herein, the term "chaotropic agent" or "chaotrope" is directed to a chemical capable of inducing a conformational change in a protein molecule, such as an IgY(ΔFc) molecule according to the invention, which is therefore often known as a protein denaturant. A chaotropic eluent will interrupt the interaction between antigen and antibody by essentially dissolving hydrophobic binding regions into the aqueous phase. According to the invention, most of the bound antibodies can be successfully eluted with any neutral buffer containing moderate concentration (>1 M) of a chaotropic agent. In most instances, removal of the chaotrope after elution will restore the native protein structure.

The eluents useful in immunoaffinity chromatography include but is not limited to 0.1 M glycine-HCl, pH 2.3; 0.1 M glycine-HCl, pH 10.0; 6 M guanidine-HCl, pH 3.0; 3.0 M potassium chloride; 5 M potassium iodide; 3.5 M magnesium chloride; 1–3 M ammonium/sodium thiocyanate and 6 M urea. With respect to the activity of the recovered antibodies, however, a moderate-ionic strength, chaotrope-containing, neutral pH buffer, such as 3 M sodium thiocyanate buffered in 20 mM MES buffer (pH 5.8) or 20 mM Tris(hydroxymethyl)-aminomethane (pH 7.5), is more suitable for practicing the invention.

The active state of the collected antibodies can be easily restored by, for example, extensive dialysis against a low-ionic strength, non-chaotrope-containing, weakly acidic buffer. The antigens immobilized on the matrix can easily restore their native conformation by washing the antigen matrix with a chaotrope-free buffer.

In the most preferred aspect of the present invention, it is provided a process for preparing IgYΔFc from egg yolk, the process comprising the steps of:

(a) immunizing a fowl hen with a selected antigen so that fowl antibodies elicited against the antigen are accumulated in egg yolk;

(b) collecting yolk antibodies by diluting egg yolk of the immunized hen with an effective amount of water at a pH of about 5–7 and a temperature of about 0° C.–60° C. to form a mixture for at least 1 hour; and (c) separating the water-soluble fraction containing the yolk antibodies from yolk granules and lipids by centrifugation under 1,500–30,000×g for 0.5–6 hour at 0° C.–60° C. or filtration through filter paper;

(d) precipitating yolk antibodies in the water-soluble fraction with ammonium sulfate or sodium sulfate;

(e) redissolving yolk antibodies with a buffer solution at a salt concentration of 1–50 mM and a pH of about 4–9; and (f) applying the dissolved yolk antibodies to a chromatographic support matrix immobilized with the antigen thereon so as to immunoadsorb yolk antibodies;

(g) washing the chromatographic support matrix with a buffer solution at a salt concentration of 1–50 mM and a pH of about 4–9;

(h) eluting the yolk antibody bound on the chromatography support matrix with a chaotropic salt at a concentration higher than 50 mM, or with a buffer at a pH lower than 4 or higher than 8 such that an eluate containing the IgY(ΔFc) antibodies is obtained.

The yolk antibody purified according to the process of the invention is a homogenous IgY(ΔFc). Purity was checked by non-denaturing sodium dodecyl sulfate polyacrylamide gel electrophoresis (SDS-PAGE) and the molecular weight of the obtained IgY(ΔFc) was confirmed to be 120 kDa. No IgY contamination was found in the gel. Because of the polyclonal nature of the antibody, the isoelectric point of the IgY(ΔFc) has a broad spectrum (5.2–7.3).

The IgY(ΔFc) purified according the method of the invention neither activate the complement system nor binds to rheumatoid factor of mammalian sera. The immunological cross-reactivity between IgY(ΔFc) and the mammalian IgG is not significant. Thus, the invention also provide a new type of antibody suitable for clinical and research uses.

The invention also provides a broad variety of clinical and research uses of the IgY(ΔFc) antibody prepared according to the invention.

For example, the present invention provides a method for immunizing an animal (which includes domestic fowls, livestock and companion animals) or human patient by administering to the patient a therapeutic amount of the the IgY(ΔFc) antibody of the present invention to protect them from various etiological agents, including microorganisms, such as bacteria, viruses, fungi, protozoa, nematodes and the like, and proteinaceous or non-proteinaceous substances, such as allergens, toxins, venoms, hormones, or any other immunogen capable of eliciting an immune response. Preferably, the purified IgY(ΔFc) antibody is administered in combination with a pharmaceutically acceptable carrier such as water, saline and the like.

The IgY(ΔFc) antibody of the present invention is also useful for detecting an etiological agent of interest, including, for example, a pathogenic or non-pathogenic organism, such as *Escherichia coli, Salmonella enterititis*, and other bacterial organisms; a hormone such as estrogen, progesterone, thyroxin and the like; a major histocompatibility complex antigen and the like; a tumor marker such as alpha-fetoprotein, prostate specific antigen and the like; a disease state marker such as C-reactive protein, ferritin and the like; in a body sample such as a fluid, tissue, cell extract and the like, that is derived from the human or animal. Using the IgY(ΔFc) antibody obtained according to this invention, an etiological agent of interest can be quantitatively or qualitatively detected by any conventional method known in the art, such as the Ouchterlony methods (MO), the single radial immuno diffusion method (SRID), the immuno electrophoresis method (IEP), the radioimmuno assay method (RIA), the enzyme-linked immuno solvent assay method (ELISA), the Western blot method (WB), the turbidimetric immunoassay method (TIA) or the particle-enhanced turbidimetric immunoassay method.

Based upon the optimal binding condition as defined above, the present invention further provides a quantitative or qualitative method of immunoassay for analyzing an etiological agent as mentioned above, in which an antibody, preferably the IgY(ΔFc) antibody purified according to the invention, raised against the etiological agent is incubated in the presence or absence of the etiological agent under the optimal binding condition. According to the present invention, the optimal condition is at pH within a range of 4–7 and under an ionic strength of lower than 50 mM. Preferably, the antibodies were allowed to interact with the etiological agent at pH within a range of 5–6 and more preferably within a range of 5.6–5.8.

A kit for conducting the above immunoassay is also provided, in which a reagent comprising a yolk antibody, preferably the IgY(ΔFc) antibody purified according to the invention, specific to an etiological agent of interest is included, wherein the immunoassay is conducted at pH 4–7 and under an ionic strength of lower than 50 mM. Preferably, the antibodies were allowed to interact with the etiological agent at pH within a range of 5–6 and more preferably within a range of 5.6–5.8.

When used in, for example, a single radial immunodiffusion method (SRID), the IgY(ΔFc) antibody according to the present invention can be formulated into a supporting medium constituted with, for example, agar, agarose, starch, polyacrylamide gel and the like, by any conventional method. For example, a supporting medium can be suspended in a buffer solution under heat, to which the IgY(ΔFc) antibody is added, and the resultant is mixed together. The resulting solution is poured onto a glass plate or into a plastic vessel, and then cooled to solidify. In order to apply the sample to be examined, a sample well is made on the resulting gel plate. Although the principle of this technique is known to those skilled in the art, the physical requirements of IgY(ΔFc) antibody-antigen interaction are stricter than those of general antibody-antigen interaction. Specifically, the duck IgY(ΔFc) antibodies bind to antigen and display precipitating properties only under the particular binding condition of the invention. The particular binding condition also works for other immunoassay methods such as, for example, the Ouchterlony method (MO) and the turbidimetric immunoassay method (TIA), in which the precipitation or agglutination of an antigen by IgY(ΔFc) antibody is regarded as an essential step.

Accordingly, one of the most preferred aspect of the present invention is to provide a method for the single radial immunodiffusion assay of antigen comprising:
(a) preparing agar gels containing egg yolk antibody in buffer solution at a salt concentration of 1–50 mM and a pH of about 5–7;
(b) punching wells in the agar and removing the plugs of agar from the wells;
(c) preparing dilutions of antigen in phosphate buffer saline; and
(d) pipetting each antigen dilution and specimens into separate wells;
(e) incubating for at least 24 hours; and
(f) measuring the diameter of the immunoprecipitin rings, which is linear correction with $\log_{10}$ concentration of antigen.

In an enzyme-linked immuno solvent assay method (ELISA) or a particle-enhanced turbidimetric immunoassay method, an antigen of interest located in a sample is captured by IgY(ΔFc) antibody immobilized on a resin test plate such as polyvinylchloride, polystyrene and the like, or a fine particle made by, for example, polystyrene latex, polyester latex, polyvinylchloride, bentonite, glass beads and the like, in an amount effective to interact with a sample that evidences the presence of the antigen of interest. In the particle-enhanced turbidimetric immunoassay method, the captured antigen is then directly detected in terms of changes in turbidity. The turbidity changes were measured at 320–900 nm. In the enzyme-linked immuno solvent assay (ELISA), the captured antigen is further detected by an antibody conjugated with a signaling substance.

PREFERRED EMBODIMENTS FOR PRACTICING THE INVENTION

The following Examples are given for the purpose of illustration only and are not intended to limit the scope of the present invention.

EXAMPLE 1

Immunization Procedure for Stimulation of Specific Antibody Production

Twelve, 16-week old, domestic ducks (*Anas platyrhynchos var. domestica*) were individually housed for antibody and egg production. The ducks received an initial subcutaneous injection of 1–5 mg/ml of human C-reactive protein (CRP; purified from human ascites) in phosphate buffer, pH 7.5 emulsified with an equal volume of complete Freund's adjuvant. The concentration of the antigen used was generally in the range of 1 to 5 mg/ml. After the initial injection, young hens received four additional injections of 1–5 mg of antigen every two weeks. One week later, eggs began to be collected, labeled and stored at 4° C. until processed for extraction and purification of antibody. The booster procedure was repeated every four weeks during the experiment. Blood was sampled at the seventh day after each booster injection. Each blood sample was centrifuged and the resulting serum was collected.

EXAMPLE 2

The Physical Requirements for Precipitation of Duck Antibodies

In this example, the effects of pH and salt on the precipitation of duck antibodies were investigated. Agarose powder was suspended with heat in 0.02 M phosphate buffer solutions varying in pH and concentration of sodium chloride. The agarose solution was cooled to about 56° C. to which 0.5 ml of antigen solution containing 0.4 mg/ml of the purified CRP was added with stirring. The solution was poured into a plastic vessel and allowed to cool. Wells for duck antisera were made on the plate at regular intervals. An antiserum collected in example 1 was diluted 1 and 2 folds with the phosphate buffer used for preparing the plate, and 2 μl of the original and diluted antisera were loaded into separate wells in the agarose plate.

In the first set of the experiment, the CRP-containing agarose gels were prepared at pH 4, 5, 6, 7, 8 and 9, respectively. 2 μl of the original and diluted antiserum was loaded into separate wells in these agarose. After a 48-hour incubation, the diameter and sharpness of the immunoprecipitin ring was determined as listed in Table 1.

TABLE 1

Diameter of the immunoprecipitin ring at different pH condition

| Buffer in agarose gels | Antisera dilution | | |
|---|---|---|---|
| | 1:1 | 1:2 | 1:4 |
| 20 mM PB, pH 4.0 | — | — | — |
| 20 mM PB, pH 5.0 | 6.6 | 4.9 | 3.9 |
| 20 mM PB, pH 6.0 | 6.3 | 4.7 | 3.7 |
| 20 mM PB, pH 7.0 | 6.0 | 4.5 | 3.5 |
| 20 mM PB, pH 8.0 | 5.9 | 4.4 | 3.4 |
| 20 mM PB, pH 9.0 | 5.9 | 4.4 | 3.4 |

As shown in Table 1, no immunoprecipitin rings was observed in agarose plate of pH 4.0. Although the immunoprecipitin rings were visible in agarose plates of pH over 5.0, the precipitin was gradually fade out in sharpness as pH value increased up to 7. Best precipitation, based on the sharpness and size of the precipitin rings, was obtained at pH 5.0. The result indicates that duck antibodies bind properly with an antigen at pH 5.0.

In the second set of the experiment, the above procedure was repeated except that the agarose gels were prepared in 20 mM phosphate buffer, pH 5.0 containing 0.5, 1.0 or 1.5 M of sodium chloride, respectively. After incubation, the precipitatin rings were less distinct than those shown on the agarose plate free of sodium chloride (data not shown). The result indicates that the precipitation of duck antibodies can be remarkably inhibited in the presence of a salt.

Taking together, the agarose plates prepared in 20 mM phosphate buffer at pH of 5.0 may be more suitable for formation of the precipitation of duck antibodies.

EXAMPLE 3

Assay of Antibody Titer Potencies

The titer potency of the anti-sera obtained in example 1 was determined by SRID. The CRP-containing agarose plates were prepared using 20 mM phosphate buffer (pH 5.0) as described in example 2. 2 μl of the anti-sera obtained in example 1 were individually loaded into separate wells punctured on the plates. After incubation, an immunoprecipitin ring was formed around the well, and the diameter of the ring, which is relevant to the titer potencies of the loaded anti-sera, was determined.

EXAMPLE 4

Extraction of Antibodies from Duck Yolks

The yolks collected from the eggs laid by the hyperimmunized ducks of example 1 were thoroughly washed by a weak jet of distilled water, to thereby remove albumen. The volume of yolk was measured and then mixed thoroughly with distilled water in an amount of ten times the measured amount of yolk. The mixture was then held for at least two hours under 4° C., and subsequently centrifuged at 10,000 rpm in a Hitachi CR22F centrifuge for one hour. A pale supernatant layer and a semi-solid pliable layer were formed in centrifuge tubes. The supernatant layer was carefully collected, to which pulverized ammonium sulfate was added with gentle stirring to a final concentration of 25 g ammonium sulfate per 100 ml yolk extract, so that the yolk antibodies were completely salted out. The precipitate was collected by centrifugation at 10,000 rpm for 30 minutes at 4° C. After decanting the supernatant, the resulting pellet was redissolved in a suitable buffer, and dialyzed against the buffer to remove the residual ammonium sulfate. Twenty batches of the crude antibodies obtained by this procedure were pooled and stored at 4° C. for further experiments. The antibody titer potency of the pool was 6.1 mm in diameter of the immunoprecipitin ring under the SRID assay as described in example 3.

EXAMPLE 5

Covalent Attachment of the Antigen to Cyanogen Bromide-Activated Agarose Matrix

A CRP solution was prepared in 0.1 M carbonate buffer, pH 8.5 at a concentration of 5 mg/ml. CNBr-activated SEPHAROSE™ 4B purchased from Pharmacia was washed initially with 1 mM cold HCl in an amount of ten times the matrix volume and allowed to react with the CRP solution in an amount of two times the matrix volume of at 4° C. overnight. Coupling efficiency was calculated as the amount of the coupled protein (in $A_{280}$ units) divided by the starting amount of the protein ($A_{280}$). The result shows that the coupling efficiency of CNBr-activated SEPHAROSE™ 4B was within the range of 80–85%. For later use, the antigen matrix was suspended in a solution of 0.5 M ethanolamine in 20 mM Tris-HCl (pH 8.5) in a ratio of 1:1 (v/v) for 2 hours at 4° C. to block remaining protein-reactive sites. The antigen matrix was then washed with PBS containing 0.02% sodium azide and stored at 4° C.

EXAMPLE 6

Immunoaffinity Purification of Yolk Antibodies

In the following example 6–8, the duck antibodies obtained in example 4 and the antigen matrix prepared in example 5 were used to demonstrate the suitable binding condition for immunoaffinity purification of the yolk antibodies. One ml of the antigen matrix was filled in a conventional column and soaked in one of the binding buffer listed in Table 2. The antigen matrix was allowed to react with 0.25 ml of the antibodies formulated in the same binding buffer. The antigen matrix was washed with the binding buffer until the effluent was substantially free of protein. Bound antibodies were eluted immediately with 4M guanidine-HCl, and the optical density thereof was measured at 280 nm after a complete dialysis. The binding capability of duck antibody in different binding buffer is represented by the amount of antibody in the final eluate as shown in the following Table 2.

TABLE 2

Amount of Antibody binding on Antigen Matrix Under Different Condition

| Binding Buffer | Antibody Content in The Eluate ($A_{280}$ unit × ml) |
|---|---|
| 20 mM PB, pH 4 | 0.26 |
| 20 mM PB, pH 5 | 0.43 |
| 20 mM PB, pH 6 | 0.39 |
| 20 mM PB, pH 7 | 0.32 |
| 20 mM PB, pH 8 | 0.29 |
| 20 mM PB, pH 9 | 0.25 |

It can be seen that a comparatively large amount of duck antibodies is bound under a weak acid environment.

EXAMPLE 7

Example 6 was repeated except that the pH value of the binding buffer was adjusted to 5.2, 5.4, 5.6, or 5.8 in each test. The results are shown in Table 3 as follows.

TABLE 3

Amount of Antibody binding on Antigen Matrix Under Different Condition

| Binding Buffer | Antibody Content in The Eluate ($A_{280}$ unit × ml) |
|---|---|
| 20 mM PB, pH 5.2 | 0.45 |
| 20 mM PB, pH 5.4 | 0.46 |
| 20 mM PB, pH 5.6 | 0.53 |
| 20 mM PB, pH 5.8 | 0.54 |

In Table 3, an environment of pH 5.6–5.8 appears most suitable for the binding of the duck antibodies.

EXAMPLE 8

Example 7 was repeated at pH 5.8 except that the phosphate binding buffer was replaced with a MES buffer or a Bis-Tris buffer. The result is shown in Table 4.

TABLE 4

Amount of Antibody binding on Antigen Matrix Under Different Condition

| Binding Buffer | Antibody Content in The Eluate ($A_{280}$ unit × ml) |
|---|---|
| 20 mM PB, pH 5.8 | 0.54 |
| 20 mM MES, pH 5.8 | 0.68 |
| 20 mM Bis-Tris, pH 5.8 | 0.63 |

The result demonstrates that 20 mM MES buffer adjusted to pH 5.8 is the most suitable binding buffer for immunoaffinity purification of duck antibody.

EXAMPLE 9

Elution Efficiency

Example 6 was repeated by using 20 mM MES buffer (pH 5.8) as the binding buffer, except that 1–3 M sodium thiocyanate (pH 7.5) was utilized as a chaotrope in the eluent in comparison with 4 M guanidine-HCl. The elution efficiency of 4 M guanidine-HCl is functionally defined to be 100% as a reference standard. Relative elution efficiencies of the other eluents were determined by dividing the $A_{280}$ unit eluted with each eluent by that with 4 M guanidine HCl. The result is shown in Table 5.

TABLE 5

Efficiency of Eluents

| Eluent | Efficiency |
|---|---|
| 4 M guanidine-HCl, pH 8.0 | 100 |
| 3 M sodium thiocyanate, pH 7.5 | 95 |
| 2 M sodium thiocyanate, pH 7.5 | 70 |
| 1 M sodium thiocyanate, pH 7.5 | 55 |

It can be seen from Table 5 that 3 M sodium thiocyanate, which eluted about 95% of the bound antibody from the antigen matrix, is almost as effective as 4 M guanidine-HCl.

EXAMPLE 10

Figure 1:
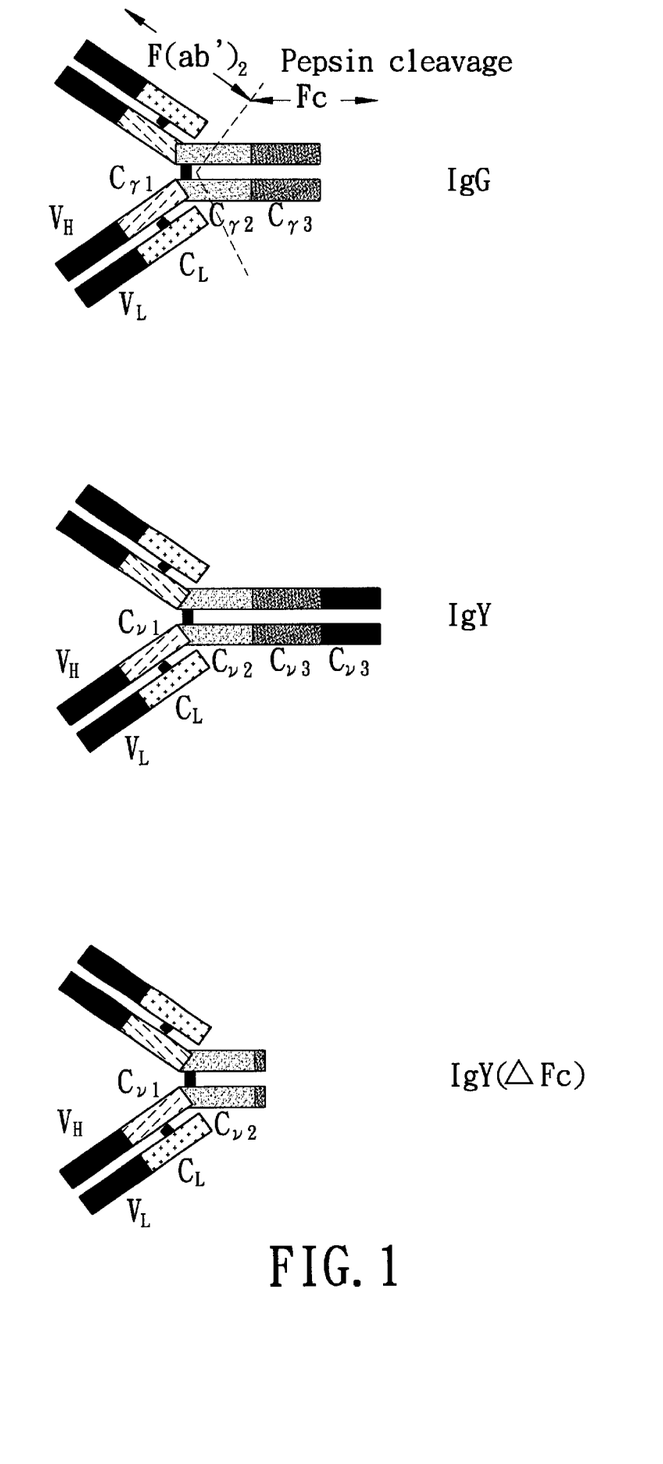
FIG. 1 is a schematic diagram showing a representative primate IgG and the duck IgY isoforms.
Figure 2:
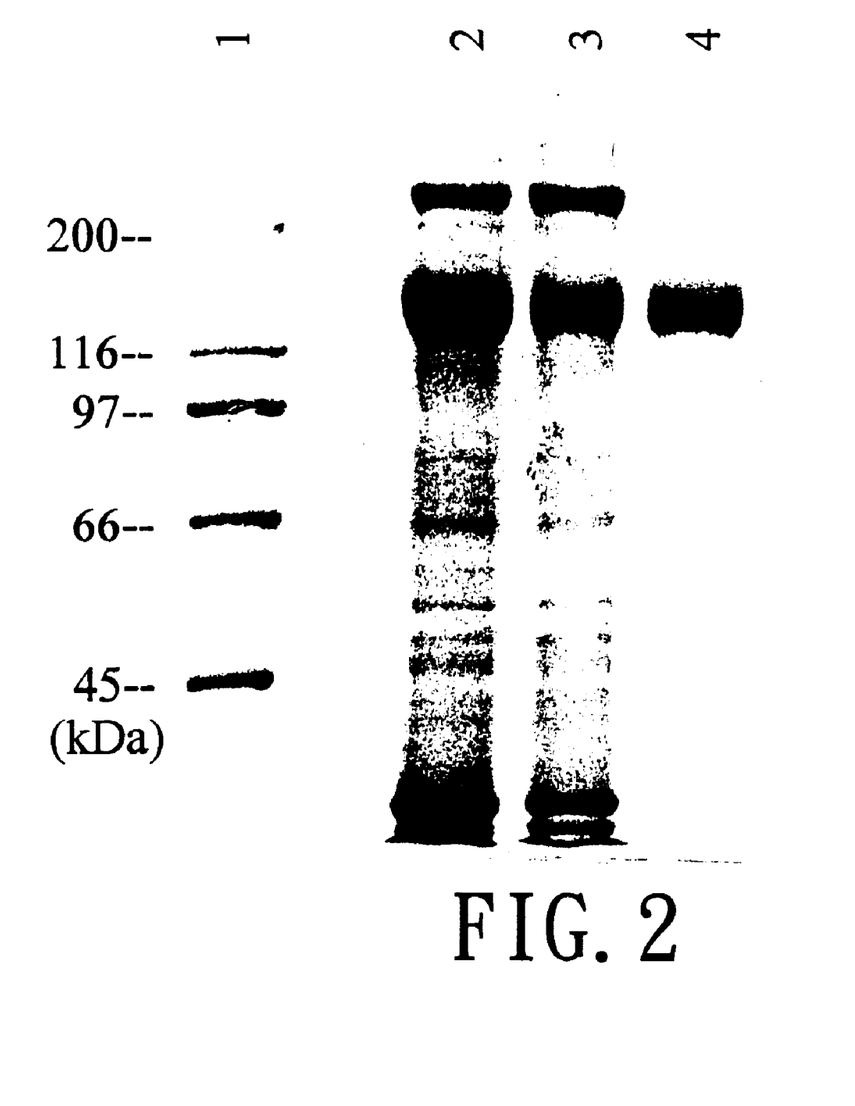
FIG. 2 shows the duck yolk antibody prepared in this invention run on an SDS-polyacrylamide gel and stained with Coomassie Blue: a molecular weight marker in lane 1; the crude antibody extract in lane 2; the flow through of the crude antibody extract after immunoaffinity chromatography in lane 3; and the affinity purified antibodies in the eluate in lane 4.

Purity and Activity of Duck Antibodies Immunoaffinity Purified on an Antigen Matrix In order to examine the composition of the antibody manufactured according to the present invention, analytical SDS-PAGE was performed on an 8% non-reducing acrylamide gel, in which 60 μg of crude antibody (Lane 2) and 40 μg of the flow through harvested in Example 3 (Lane 3) and 20 μg of the antibody product eluted by 3M sodium thiocyanate (pH 5.8) in Example 9 (Lane 4) were loaded. The result is shown in FIG. 1.

The crude product and the flow through both exhibit two predominant bands of 180 kDa and 120 kDa (these sizes are estimated from molecular weight marker in Lane 1) which correspond to the relative mobility of the duck IgY and IgY(ΔFc), respectively. On the other hand, the affinity-purified antibodies are constituted by IgY(ΔFc) antibody which is represented by a single band on the gel. These results evidence that the process of the present invention is an excellent strategy to isolate the desired IgY(ΔFc) antibodies from the pool of the immunoglobulin mixture constituted by both IgY and IgY(ΔFc). Almost all of the IgY antibodies failed to bind on the antigen matrix and remained in the flow through. Densitometric analysis of the gel indicates that over 95% of the purified antibodies is homogenous IgY(ΔFc). In addition, no more than 60% of the total protein present in the crude antibodies is IgY(ΔFc) (data not shown), and 24% of the total protein in the crude product, which is believed to correspond to the content of the desired IgY(ΔFc), can bind to antigen matrix in the affinity-purification stage.

The activity of the purified antibodies is determined by SRID as described in example 3. The diameter of the immunoprecipitin ring of the purified antibodies is 5.9, only slightly less than 6.1 of the crude antibodies.

EXAMPLE 11

Determination of CRP Concentration in an SRID Method

Figure 3:
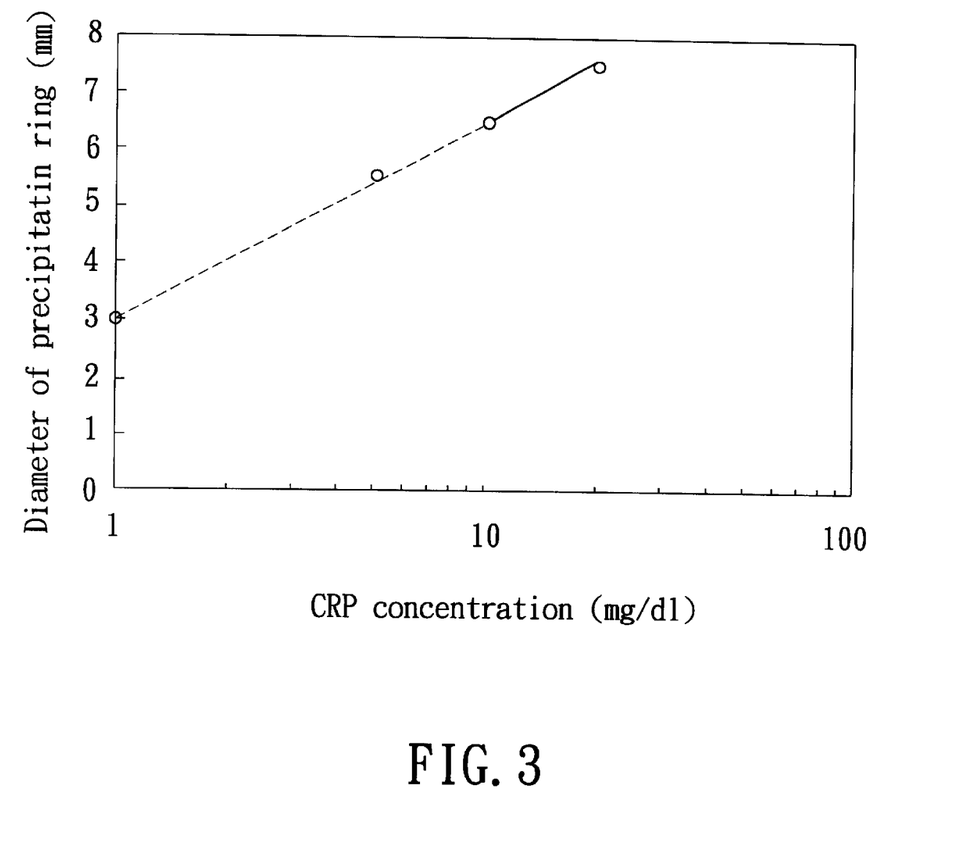
FIG. 3 shows standard curves for C-reactive protein (CRP): diameter of immunoprecipitin ring vs. C-reactive protein concentration (mg/dl, in log scale) for serum standards.
Figure 4:
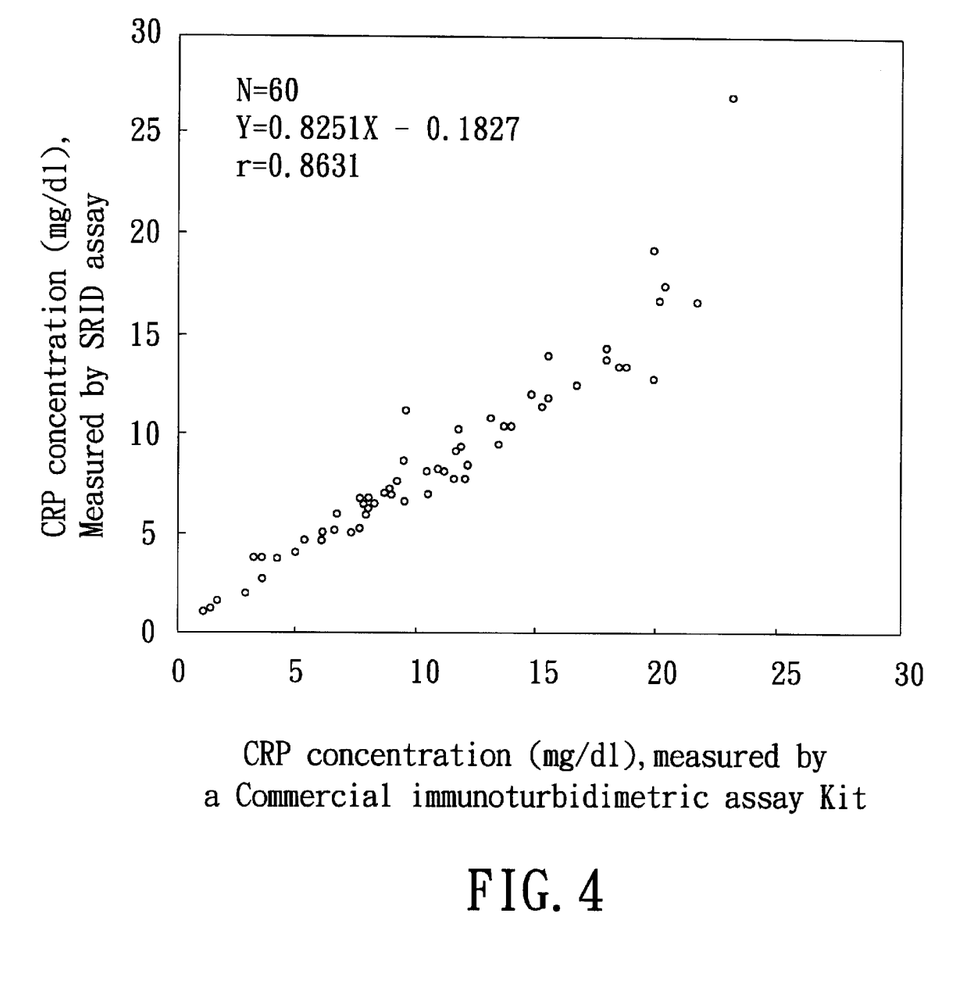
FIG. 4 shows a comparison of CRP concentrations obtained by an SRID assay according to the invention and by a commercial immunoturbidimetric assay.

Agarose plates were prepared using 20 mM phosphate buffer (pH 5.0) as described in example 2, except that the duck anti-CRP antibody affinity-purified in example 10 was added therein in replace of CRP until a final concentration of 10 μg/ml is reached. 2 μl doses of human serum from CRP-positive donors were individually loaded into separate wells punctured on the plates at regular intervals, and the plates were incubated for 48 hours. The diameter of the immunoprecipitin rings was measured and plotted against $log_{10}$ concentration of CRP standards to give a standard curve. Linearity was observed throughout the entire measuring range as shown in FIG. 3. The CRP concentration in unknown samples can be estimated by interpolation of the standard curve. The result obtained by the present SRID method is in perfect agreement with that measured by a commercial CRP-latex kit purchased from Denka Seiken Co., Ltd., 3-4-2 Nihonbashi Kayabacho, Chuo-ku, Tokyo, Japan (FIG. 4).

EXAMPLE 12

Determination of CRP Concentration in an ELISA Method

Figure 5:
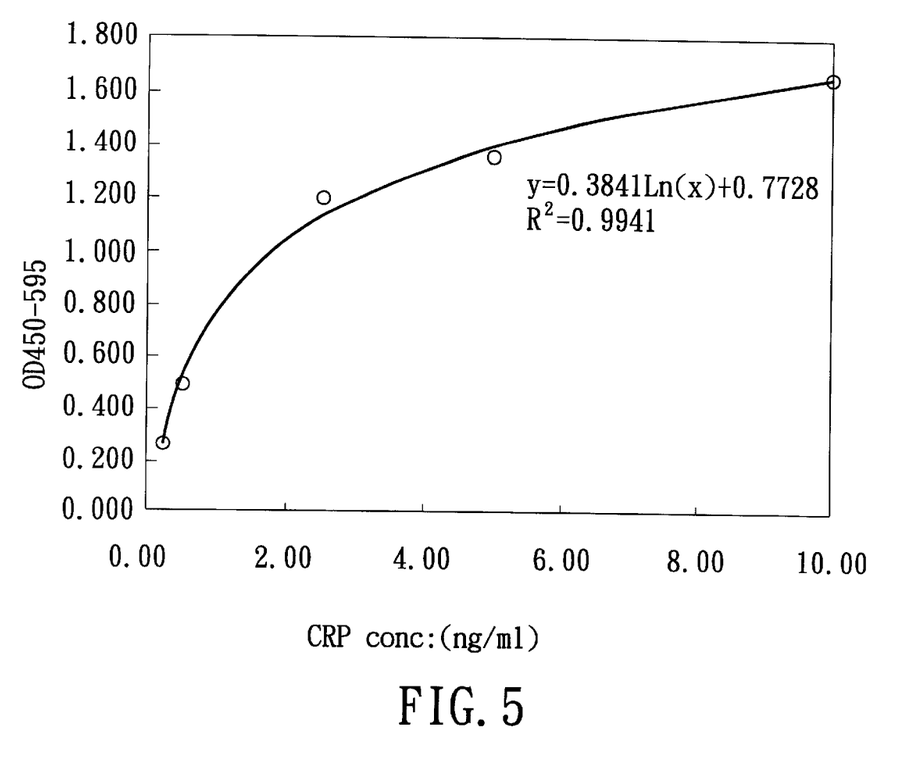
FIG. 5 demonstrates an ELISA assay, in which the IgY (ΔFc) antibody according to the present invention is used to determine the concentration of CRP.

The duck anti-CRP antibody affinity-purified in example 10 was diluted with a coating buffer (20 mM phosphate buffer, pH 8.2) to a final concentration of 16 μg/ml. 100 μl aliquots of the resulting solution were then dispensed into each well of an ELISA plate (purchased from Costar Corporation). The plate was incubated at 4° C. overnight or at 37° C. for 3 hours. At the end of the incubation, 200 μl of a blocking agent (1% nonfat milk in the coating buffer) was loaded in each well to stop coating IgY(ΔFc) on the plate. Serially diluted CRP was allowed to interact with the coated duck antibody in a reaction buffer (140 mM NaCl in 20 mM Tris buffer) at room temperature for 30 minutes. Subsequently, the plate was washed thoroughly with a washing buffer (reaction buffer containing 0.05% tween-20). A dose of a goat-anti-CRP antibody (available from Good Biotech Corp.) diluted in the reaction buffer was added to each well and the plate was incubated for 30 minutes, then washed thoroughly with the washing buffer. Next, a dose of a HRP-conjugated rabbit-anti-goat IgG (Sigma) diluted in the reaction buffer was added to each well and the plate was incubated at room temperature for additional 30 minutes, then washed thoroughly with the washing buffer. 100 μl of o-phenylenediamine dihydrochloride (Sigma) was added to each well as a substrate for the conjugated enzyme, and the plate was incubated at room temperature for 15 minutes. The reaction was quenched by 100 μl of IN $H_2SO_4$. The absorbance of each well at 450 nm was measured and plotted in FIG. 5. The sensitivity of this assay can be up to 2.5 ng/ml (O.D.>1). R-square can be up to 0. 9941.

EXAMPLE 13

Determination of CRP Concentration in Particle-enhanced TIA Method ( LAT, Latex Immunoturbidimetric Assay)

Coupling of anti-CRP IgY(ΔFc) onto latex particles was carried out at 4° C. for 2 hours in a reaction mixture containing: 100 μl of 10% (w/v) latex suspension, 400 μl of 20 mM Tris buffer (pH7.2), 10 mg/ml of the duck anti-CRP antibody purified in example 10 and 0.1% sodium azide. 5 ml of 20 mM Tris buffer (pH7.2) containing 1% bovine serum albumin (BSA; purchased from Sigma) was added to the latex-IgY(ΔFc) mixture, and the resulting suspension was incubated at 4° C. for 1.5 hours with stirring. After centrifugation at 15,000 rpm at 4° C. for 1 hour, the collected pellet was re-suspended in 5 ml of 20 mM Tris buffer (pH7.2) containing 1% BSA for later use.

Figure 6A:
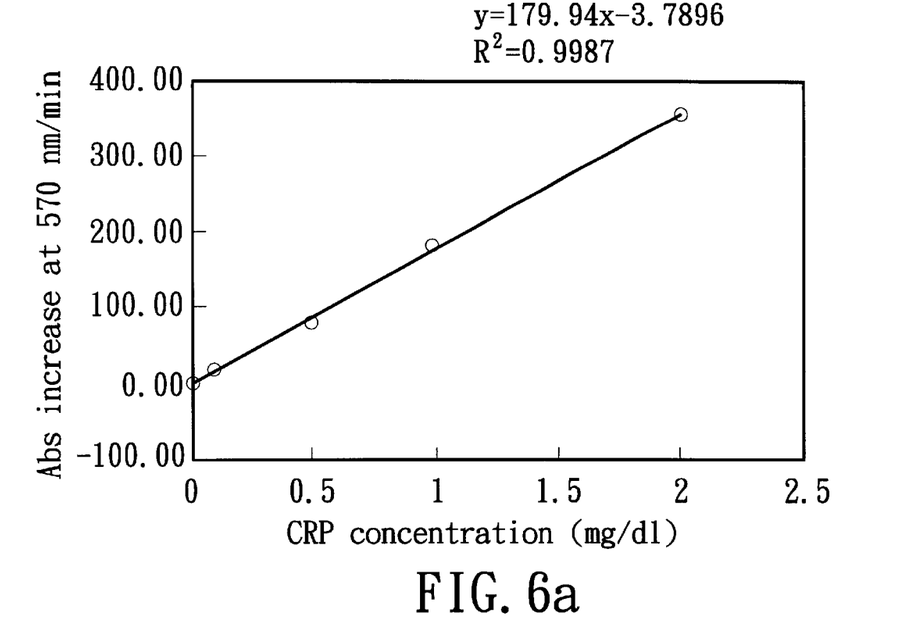
FIGS. 6a–b demonstrate a particle-enhanced turbidimetric immunoassay, in which the IgY(ΔFc) antibody according to the present invention is coupled with a latex particle and used to determine the concentration of CRP.
Figure 6B:
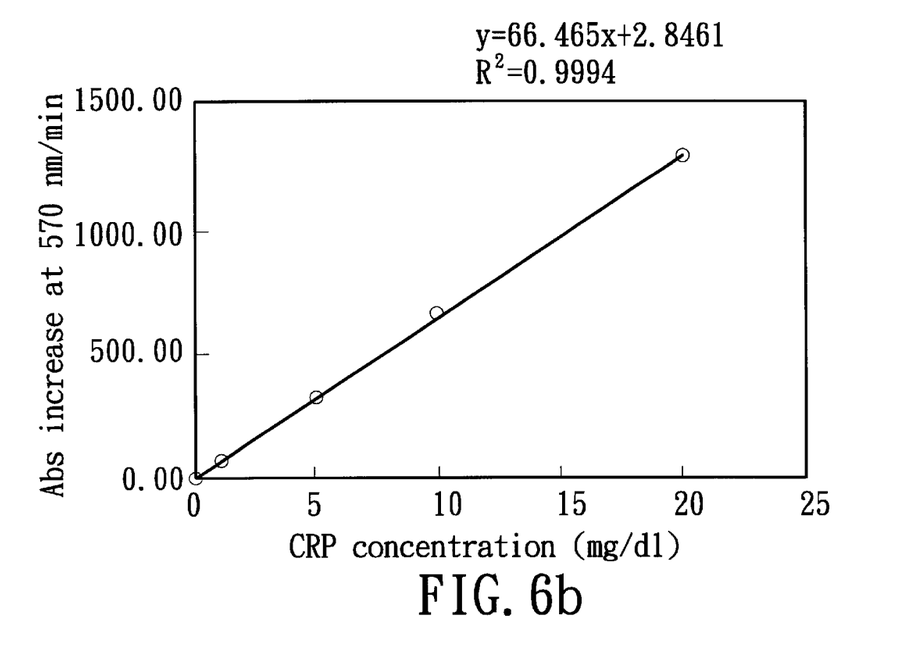

The CRP-containing calibrator serum was used as a standard antigen at the following concentrations: 0, 1, 5, 10 and 20 mg/dl in high range and 0, 0.5, 1, 1.5 and 2 mg/dl in low range. Two additional reagents were R1: 20 mM Tris buffer (pH 7.2) and R2: the IgY(ΔFc)-coupled latex suspension in R1. The increment in absorbance (at 570 nm) as a result of mixing R2 with the standard antigen was measured over time in a Hitachi 7020 turbidimetric Autoanalyzer, and the data thus obtained were plotted against the low and high ranges of the CRP concentrations, as shown in FIGS. 6a and 6b, respectively. The CRP concentration in unknown samples can therefore be estimated by interpolation of the standard curve.

All patents and literature references cited in the present specification are hereby incorporated by reference in their entirety. In case of conflict, the present description, including definitions, will prevail.

While the invention has been described with reference to the above specific embodiments, it should be recognized that various modifications and changes, which will be apparent to those skilled in the relevant art, may be made without departing from the spirit and scope of the invention.

I claim:

1. A method of separating IgY(ΔFc) from IgY, the method comprising:

(a) providing a pool of antibodies that includes an IgY that has an Fc region and an IgY(ΔFc) that lacks an Fc region, the IgY and the IgY(ΔFc) both being raised by immunization of an anseriform bird with a specific antigen;

(b) passing the pool over an antigen matrix that has the specific antigen immobilized thereto with a binding buffer having a pH value ranging from pH 4 to pH 7 and an ionic strength of less than 50 mM; and (c) washing the IgY but not the IgY(ΔFc) from the antigen matrix with the binding buffer, thereby separating the IgY(ΔFc) from the IgY.

2. The method of claim 1, further comprising (d) dissociating the IgY(ΔFc) from the antigen matrix.

3. The method of claim 1, wherein the binding buffer has a pH in the range of pH 5 to pH 6.

4. The method of claim 3, wherein the binding buffer has a pH in the range of pH 5.6 to pH 5.8.

5. The method of claim 3, wherein the binding buffer includes a buffering agent selected from the group consisting of a phosphate buffer, a (2-[N-morpholino]ethanesulfonic acid) buffer and a bis-Tris buffer.

6. The method of claim 5, wherein the buffering agent is (2-[N-morpholino]ethanesulfonic acid) buffer.

7. The method of claim 2, wherein the IgY(ΔFc) are dissociated from the antigen matrix by a chaotropic salt.

8. The method of claim 7, wherein the chaotropic salt includes at least 4 M guanidine-HCl or 1–3 M sodium thiocyanate.

9. The method of claim 8, wherein the IgY(ΔFc) are dissociated from the antigen matrix by a pH of lower than 4 or higher than 8.

10. The method of claim 1, wherein the anseriform bird is a duck.

11. The method of claim 1, wherein the antigen matrix comprises crosslinked agarose or crosslinked dextran.

* * * * *